United States Patent [19]

Miyao et al.

[11] Patent Number: 5,422,374
[45] Date of Patent: Jun. 6, 1995

[54] THERAPEUTIC AGENT FOR SLEEP APNEA

[75] Inventors: Setsuko Miyao; Kouhei Miyao; Tateo Nishimura, all of Tokyo, Japan

[73] Assignee: Nisshin Flour Milling Co., Ltd., Tokyo, Japan

[21] Appl. No.: 960,369
[22] PCT Filed: Jul. 25, 1990
[86] PCT No.: PCT/JP90/00947
  § 371 Date: Mar. 8, 1993
  § 102(e) Date: Mar. 8, 1993
[87] PCT Pub. No.: WO92/01448
  PCT Pub. Date: Aug. 6, 1992

[51] Int. Cl.$^6$ ............................................. A61K 31/12
[52] U.S. Cl. ..................................... 514/690; 514/675; 514/678
[58] Field of Search ........................ 514/690, 678, 675

[56] References Cited

U.S. PATENT DOCUMENTS

| | | | |
|---|---|---|---|
| 4,599,232 | 7/1986 | Bertelli | 424/94 |
| 4,684,520 | 8/1987 | Bertelli | 424/94.10 |
| 4,751,241 | 6/1988 | Motoyama et al. | 514/532 |
| 4,778,798 | 10/1988 | Brasey | 514/277 |

OTHER PUBLICATIONS

Chemical abstracts 88(25): 183027y, 1977, (Pichugin et al.).
"The Merck Index" (11th Ed.), Budavari et al. (Eds.), Merck and Co., Inc., Rahway, N.J., 1989, p. 1549.
European Neurology, 28(2), 1988, Tatsumi, C. et al: "Mitochondrial Encephalomyopathy with Sleep Apnea", pp. 64–69.
Patent Abstracts of Japan, No. 14459 (C-0767), Oct. 4, 1990, JP-A-21 88 523, Jul. 24, 1990.

*Primary Examiner*—Raymond Henley, III
*Assistant Examiner*—M. Moezie
*Attorney, Agent, or Firm*—Oblon, Spivak, McClelland, Maier & Neustadt

[57] ABSTRACT

Administration of ubidecarenone is effective for the therapy of sleep apnea. It is given at a dose of 1–3,000 mg per day in adults. It is especially effective to administer ubidecarenone to the patient before bed at a dose of 2–50 mg.

7 Claims, No Drawings

THERAPEUTIC AGENT FOR SLEEP APNEA

This application is a 371 of PCT/JP90/00947 filed July 25, 1990.

TECHNICAL FIELD

This invention relates to pharmaceutical compositions for the treatment of sleep apnea.

BACKGROUND ART

Sleep apnea is a disease in which apnea occurs during sleep without subjective symptom. It is more prevailing in male middle- and old-aged persons in their forties and fifties and approximately one per 100 persons is reported to suffer from the disease. In the disease there is repeated many times in sleep a sequence of 20–40 second's apnea, about 10 second's pneusis and 20–40 second's apnea. For example, approximately 400. occurrences of apnea during a 6.5-hour sleep, corresponding to a total apneic time of approximately 4 hours are observed. As a result, there occur phenomena such as daytime sleepiness to cause a trouble in driving or working, and when conditions are severer, loss of energy or appetite, swelling in the lower part of body and shortness of breath. Increase in leucocyte number, development of polycythemia and even cardiomegaly are then associated. Furthermore, decrease in oxygen concentration in blood is induced, which can be a cause of sudden death. The disease are observed not only in adults of middle or advanced age but also in infants, and may be an indirect cause of hypertension, cardiac insufficiency and arrhythmia.

Therapy currently adopted for the disease include bodyweight reduction (the frequency in obese people is as high as 83%), pressure application through the nose (CPAP), surgical operation (tonsillectomy or adenoidectomy) and use of a drug such as acetazolamide. Although drug administration is the simplest treatment among them, there have been found no effective drugs currently in use.

DISCLOSURE OF THE INVENTION

As a result of extensive studies on drugs for the treatment of sleep apnea, we have discovered pharmaceutical compositions which are capable of producing excellent results.

Thus the invention relates to a therapeutic agent for sleep apnea which comprises a pharmaceutical composition containing an effective amount of ubidecarenone and pharmaceutical carriers.

The active ingredient for the present invention, ubidecarenone, which is also called coenzyme $Q_{10}$, is a constituent of the mitochondrial lipids in cells and is reported to participate in oxidation-reduction reactions as a constituent in the ATP production-conjugating electron transport system. Because of less adverse reactions, it is now in wide use as a myocardial activator for the improvement of symptoms associated with slight or moderate congestive heart failure and is under basic therapy (edema, pulmonary congestion, hepatic swelling and angina pectoris).

The pharmaceutical compositions of the invention are prepared by combining ubidecarenone with appropriate pharmaceutical carriers (including conventional pharmaceutical adjuvants such as diluent, binder, filler, disintegrating agent, flavor, colorant, lubricant or preservative).

The compositions are preferably formulated to a unit dosage form and made an adequate form for medical use.

A dosage of ubidecarenone depends upon conditions of the patient. It also depends particularly upon patient's capacity in absorbability of the drug, as well as frequency and route of administration.

Ubidecarenone is formulated so as to be administered by any route. For example, it is in the form for oral or rectal administration. If desired, it may be designed for a formulation sustained-releasing ubidecarenone.

The composition may be, for example, in the form of tablets, capsules, packs, powders, granules, troches or suppositories.

For example, the composition preferable for oral administration may contain conventional additives such as binder (e.g., syrup, gum arabic, gelatin, sorbitol, tragacanth or polyvinylpyrrolidone); filler (e.g. lactose, sucrose, corn starch, calcium phosphate, sorbitol or glycerin); disintegrating agent (e.g. starch, polyvinylpyrrolidone, sodium starch glycolate or microcrystalline cellulose); lubricant for tableting (e.g. magnesium stearate) or pharmaceutically acceptable hardener (e.g. sodium laurylsulfate).

Solid compositions may be prepared by a conventional method including blending, filling and tableting. Repeated blending operations enable distribution of ubidecarenone uniformly throughout the composition using a large amount of fillers. When the composition is in the form of tablets, powders or troches, any of carriers preferable in the formulation of solid pharmaceutical compositions may be used, for example, magnesium stearate, starch, glucose, lactose, sucrose, powdery rice and chalk. The tablets are coated by a conventional pharmaceutical technique. The composition may also be, for example, in the form of digestive capsules such as a gelatin capsule, if desired, together with carriers and other additives.

Liquid compositions for oral administration include, for example, emulsions, syrups or elixirs.

Especially in order to obtain high bioavailability of ubidecarenone, it is preferable to use a mixture of ubidecarenone and polyglycerol.

As described above, the dosage of ubidecarenone is variable depending upon symptoms of the patient as well as frequency and route of the administration. The unit dosage form contains generally 1–1,000 mg, preferably 30–500 mg, and particularly 50, 100, 150, 200, 250, 300, 350, 400, 450 or 500 mg of ubidecarenone. The composition is given once or more times a day, for example, twice, three or four times a day. The prophylactic daily dose in adults weighing 70 kg is usually in the range of 1–3,000 mg. The unit dosage form may also contain 1–20 mg of ubidecarenone and, if desired, may be given in plural numbers to provide a daily dose as defined above.

The pharmaceutical compositions of the invention are used for the therapy of sleep apnea. Administration may be before bed orally at a dose of 2–50 mg, preferably 5–20 mg of the active ingredient, ubidecarenone.

The pharmaceutical compositions of the invention show no toxicity when given at the doses in the abovementioned range.

EXAMPLE

Examples of the invention will be given below.

Example 1

Ten patients of sleep apnea were given a soft capsule containing 10 mg of ubidecarenone before bed, respectively.

Observation of the patients during sleep revealed that no apneic symptom was recognized in 8 patients of the ten. Moreover, there occurred neither doze nor feeling of malaise in daytime.

Example 2

Ten patients who had been diagnosed as sleep apnea were given soft capsules each containing 10 mg of ubidecarenone (Decasoft manufactured by Nisshin Flour Milling Co., Ltd.) at a dose of one capsule after supper for a period of days shown below.

Clinical symptoms of the patients were observed, and apnea index (times/hour) was also measured before and after administration.

Results of the clinical test are shown below.

| Patient | Age | Clinical symptom | Days of administration | Types | Time Measured | Frequency of apnea (times) | Longest duration of apnea (second) | Apnea index (times/hour) |
|---|---|---|---|---|---|---|---|---|
| K. O | 55 | Somnolence (+) | 7 | CM | 6h00m | 196 | 139 | 32.6 |
| | | | | | 3h31m | 83 | 31 | 23.6 |
| T. S | 55 | No subjective symptom Somnolence (−) | 10 | O | 6h44m | 112 | 79 | 16.6 |
| | | | | | 6h14m | 76 | 87 | 12.1 |
| H. N | 64 | Feeling of a lump in the throat Blood pressure 130/80 → 110/80 | 3 | O | 7h20m | 124 | 84 | 16.9 |
| | | | | | 6h49m | 94 | 46 | 13.7 |
| K. I | 59 | Insomnia | 7 | CM | 6h56m | 328 | 140 | 47.3 |
| | | | | | 5h52m | 185 | 74 | 31.5 |
| T. G | 48 | Daytime hypersomia, Snoring, Hypertension | 3 | O | 6h34m | 324 | 89 | 49.3 |
| | | | | | 6h51m | 231 | 72 | 33.7 |
| A. O | 58 | Daytime somnolence, Snoring, Hypertension | 3 | O | 6h45m | 193 | 62 | 28.5 |
| | | | | | 8h19m | 224 | 73 | 26.9 |
| T. H | 57 | Insomnia, Snoring | 3 | O | 9h19m | 142 | 29 | 15.2 |
| | | | | | 7h10m | 3 | 15 | 0.4 |
| K. W | 39 | Hypersomnia, Snoring | 3 | O | 5h56m | 282 | 66 | 47.5 |
| | | | | | 2h19m | 96 | 32 | 41.4 |
| T. N | 61 | Insomnia, Somnolence, Hypertension, Diabetes | 3 | O | 7h38m | 178 | 79 | 23.8 |
| | | | | | 6h09m | 133 | 76 | 21.6 |
| A. T | 56 | | 3 | O | 8h22m | 180 | 113 | 21.5 |
| | | | | | 8h18m | 45 | 21 | 5.4 |

In the above table, "Types" are as follows.
O: Obstructive
C: Central
M: Mixed

"Apnea index" means frequency of apnea per hour (used for the judgment of apnea).

Data for each patient in the above table represent those measured before administration on the upper line and those measured after administration on the lower line.

As clearly seen from the above table, ubidecarenone was effective in the therapy of sleep apnea.

What is claimed is:

1. A method for reducing the frequency of sleep apnea, comprising orally administering 1–3000 mg per day of ubidecarenone to a person in need thereof, thereby reducing the frequency of apnea.

2. The method of claim 1, comprising administering 30–500 mg per day of ubidecarenone.

3. The method of claim 1, comprising administering 1–100 mg per day of ubidecarenone.

4. The method of claim 1, comprising administering 2–50 mg per day of ubidecarenone.

5. The method of claim 1, comprising administering 100–500 mg per day of ubidecarenone.

6. The method of claim 1, wherein said ubidecarenone is administered as a pharmaceutical composition containing ubidecarenone and a pharmaceutically acceptable carrier.

7. The method of claim 6, wherein said pharmaceutically acceptable carrier is polyglycerol.

* * * * *

UNITED STATES PATENT AND TRADEMARK OFFICE
CERTIFICATE OF CORRECTION

PATENT NO. : 5,422,374
DATED : June 6, 1995
INVENTOR(S) : Setsuko MIYAO, et al.

It is certified that error appears in the above-indentified patent and that said Letters Patent is hereby corrected as shown below:

On the title page, Item [87], the PCT Publishing Date should read:

--Feb. 6, 1992--

Signed and Sealed this

Fifth Day of September, 1995

Attest:

BRUCE LEHMAN

Attesting Officer     Commissioner of Patents and Trademarks